(12) United States Patent
Shekalim

(10) Patent No.: US 6,736,796 B2
(45) Date of Patent: May 18, 2004

(54) FLUID DRUG DELIVERY DEVICE

(75) Inventor: Avraham Shekalim, Nesher (IL)

(73) Assignee: Nili-Med Ltd., Haifa (IL)

( * ) Notice: Subject to any disclaimer, the term of this patent is extended or adjusted under 35 U.S.C. 154(b) by 0 days.

(21) Appl. No.: 09/991,708

(22) Filed: Nov. 26, 2001

(65) Prior Publication Data

US 2003/0100863 A1 May 29, 2003

(51) Int. Cl.[7] .................... A61M 1/00; A61M 37/00; A61M 5/00; A61M 5/20; F16K 31/02
(52) U.S. Cl. .................... 604/134; 604/31; 604/151; 604/246; 251/129.01
(58) Field of Search ................. 604/30, 31, 131, 604/132, 133, 246, 247, 248, 249, 250, 256, 151, 134, 236; 251/129.06, 129.01

(56) References Cited

U.S. PATENT DOCUMENTS

| | | | |
|---|---|---|---|
| 4,619,653 A | 10/1986 | Fischell | |
| 4,722,372 A | * 2/1988 | Hoffman et al. | 222/214 |
| 4,741,736 A | * 5/1988 | Brown | 604/134 |
| 5,053,031 A | 10/1991 | Borsanyi | |
| 5,085,562 A | 2/1992 | Van Lintel | |
| 5,097,122 A | 3/1992 | Colman et al. | |
| 5,239,319 A | 8/1993 | Miyazaki et al. | |
| 5,269,762 A | 12/1993 | Armbruster et al. | |
| 5,405,614 A | * 4/1995 | D'Angelo et al. | 604/20 |
| 5,433,351 A | * 7/1995 | Okuyama et al. | 222/214 |
| 5,462,525 A | 10/1995 | Srisathapat et al. | |
| 5,505,709 A | 4/1996 | Funderburk et al. | |
| 5,527,288 A | 6/1996 | Gross et al. | |
| 5,527,307 A | 6/1996 | Srisathapat et al. | |
| 5,637,095 A | 6/1997 | Nason et al. | |
| 5,647,853 A | 7/1997 | Feldmann et al. | |
| 5,957,890 A | 9/1999 | Mann et al. | |
| 5,993,654 A | 11/1999 | Black | |
| 6,092,695 A | * 7/2000 | Loeffler | 222/207 |
| 6,150,681 A | 11/2000 | Allen | |
| 6,247,908 B1 | 6/2001 | Shinohara et al. | |
| 6,248,093 B1 | 6/2001 | Moberg | |
| 6,309,189 B1 | 10/2001 | Rey-Mermet et al. | |
| 6,314,980 B1 | 11/2001 | Beswick et al. | |
| 6,368,314 B1 | 4/2002 | Kipfer et al. | |
| 6,422,431 B2 | 7/2002 | Pelc et al. | |

OTHER PUBLICATIONS

A high–precision piezoresistive Flow Sensor for microdosing applications; Boillat www.sensorsmag.com/articles/0900/129/main.shtml.

* cited by examiner

*Primary Examiner*—Brian L. Casler
*Assistant Examiner*—Matthew F DeSanto
(74) *Attorney, Agent, or Firm*—Mark M. Friedman

(57) ABSTRACT

A portable insulin delivery device that supplies insulin in a pre-pressurized chamber, passes the insulin through a pressure-dropping labyrinth to a flow control valve. The valve is activated by a piezoelectric actuator. This allows for precise insulin delivery. An electronic package provides for programming of basal rates and bolus. A pressure sensor relays data concerning normal operation and pressure changes that indicate problems. The processor, keypad, display, power source, fluid pressure sensor and fluid flow control actuator are housed in a base unit. A removable cartridge unit houses the pre-pressurized fluid reservoir, flow path labyrinth, and flow control valve.

12 Claims, 11 Drawing Sheets

FLUID DRUG DELIVERY DEVICE

FIELD AND BACKGROUND OF THE INVENTION

The present invention relates to fluid drug delivery devices and, in particular, it concerns a portable insulin delivery device.

There are known portable insulin delivery devices, commonly referred to as insulin pumps, that generally consist of a pump mechanism, an insulin container, a processor, and a power source for the processor and pump mechanism. The pump mechanisms of prior art generally use motor driven push rods to push a piston into the insulin containment region of the insulin container, thus forcing the insulin into a delivery tube and therefore into the patient. The inventions of prior art have gone to great lengths to devise variations of the motor driven push rod and piston assembly that is accurate, reliable, and space efficient. Disclosures representative of this case of devices will be found in U.S. Pat. Nos. 6,248,093, 5,637,095, 5,097,122, and 5,505,709. Devices based on this configuration suffer from two inherent problems, the motor and the push rod and piston assembly, as discussed in the following paragraphs.

The amount of insulin delivered to the patient is therefore controlled by the speed at which the motor turns (RPM's) and the amount of time the motor is turning. The accuracy of insulin delivery is, then, dependent on the reliability and accuracy of the motor. Variations on RPM's will cause variations in the amount of insulin delivered to the patient. Due to a limited power supply the motor is turned on and off at preset intervals. Even when the system is operating properly, the medication is delivered in "spurts" and the delivery rate is determined as an average over time.

As the motor turns, it moves a push rod, which in turn moves a piston that forces the insulin out of the container. The seal between the piston and the side of the container must be very tight in order to prevent leakage of insulin. A side effect of this tightness is the tendency of the piston to move forward at an uneven rate. That is to say, that the piston may stick and then jump forward. This uneven movement of the piston causes uneven delivery of the insulin to the patient.

The prior art has developed elaborate devices to detect and respond to occlusion and other flow rate or system malfunctions as is demonstrated in U.S. Pat. Nos. 5,097,122, 5,462,525, 4,619,653, and 5,647,853. In cases of occlusion, most commonly these devices allow the motor to continue to push against the blockage. Due the limitation of the motor, and since this happens only in cases of full occlusion, this is not a very satisfactory solution. Further, if the blockage is opened, the pressure built up in the container and delivery tube is released through the tube, thereby forcing a possibility dangerously larger than prescribed dose of insulin into the patient. One proactive approach to occlusion includes the use of "inert" cleaning fluid being pumped through the device and into the patient.

There is therefore a need for a portable insulin delivery device that is able to deliver the insulin at a substantially consistent dosage rate, quickly detect flow rate malfunction, overcome blockage with substantially no affect on the prescribed dosage or the use of non-medicative cleaning fluids, and has very low energy requirements. It would be preferable if the device had low power requirements, and was more compact and economical than devices currently in use.

SUMMARY OF THE INVENTION

The present invention is a fluid drug delivery device.

According to the teachings of the present invention there is provided, a fluid drug delivery device comprising: a) a fluid supply assembly having a chamber, a piston, and a spring element, the piston deployed within the chamber so as to define a fluid containment volume within the chamber, the spring element deployed so as to bias the piston toward the fluid containment volume so as to pressurize an amount of the fluid drug supplied within the fluid containment volume, the containment volume having a supply outlet; b) a pressure regulator having a fluid inlet in fluid communication with the fluid supply assembly, the pressure regulator also having a fluid outlet; and c) a flow control assembly in fluid communication with the pressure regulator fluid outlet.

According to a further teaching of the present invention, the flow control assembly includes: a) a flow control valve interconnected with the fluid outlet; b) a flow actuator deployed so as to regulate the flow control valve thereby varying amounts of fluid flowing through the flow control valve; c) a positioning component deployed so as to properly position the flow control valve actuator in relationship to the flow control valve; and d) a processing unit electronically interconnected with a pressure sensor and the flow actuator, the processing unit configured so as to use data from the pressure sensor to determine activation of the flow actuator.

According to a further teaching of the present invention, the pressure regulator includes an elongated pressure reduction passageway configured so as to reduce the pressure in the fluid thereby creating a pressure differential between the fluid inlet and the fluid outlet.

According to a further teaching of the present invention, at least one pressure sensor is interconnected with at least a first and a second pressure sensing points, the pressure sensing points being located at intervals along the flow reduction passage.

According to a further teaching of the present invention, the flow actuator includes a piezoelectric actuator.

According to a further teaching of the present invention, the positioning component includes a rotatable adjustment shaft manually rotated by a thumb-wheel, the shaft and the thumb-wheel being connected by way of an over-running clutch mechanism configured to allow the thumb-wheel to continue turning while discontinuing rotation of the shaft when the flow actuator is properly positioned in relationship to the flow control valve.

According to a further teaching of the present invention, the processing unit is further interconnected to an alarm unit, the processing unit using data from the pressure sensor to determine activation of the alarm unit.

According to a further teaching of the present invention, the flow actuator, the manual positioning component, the pressure sensor, and the processing unit are housed in a base unit further including a processing unit display, a processing unit input keypad, and a power supply.

According to a further teaching of the present invention, the fluid supply assembly, the flow reduction passage, and the flow control valve, are housed in a removable cartridge unit.

There is also provided according to the teachings of the present invention, a fluid drug delivery device comprising: a) a fluid supply assembly; b) an elongated pressure reduction passageway having a fluid inlet in fluid communication with the fluid supply assembly, and a fluid outlet, the elongated passageway configured so as to reduce pressure in the fluid thereby creating a pressure differential between the fluid inlet and the fluid outlet; c) at least one pressure sensor interconnected with a first and a second pressure sensing points, the pressure sensing points located at intervals along the elongated passageway so as to discern a pressure differential between the first and second pressure sensing points; and d) a flow control assembly responsive to the pressure sensor and controlled in response to the pressure differential.

According to a further teaching of the present invention, the flow control assembly includes: a) a flow control valve interconnected with the fluid outlet; b) a flow actuator deployed so as to regulate the flow control valve thereby varying amounts of fluid flowing through the flow control valve; c) a positioning component deployed so as to properly position the flow control valve actuator in relationship to the flow control valve; and d) a processing unit electronically interconnected with a pressure sensor and the flow control valve actuator, the processing unit configured so as to use data from the pressure sensor to determine activation of the flow control valve actuator.

According to a further teaching of the present invention, the flow actuator includes a piezoelectric actuator.

According to a further teaching of the present invention, the positioning component includes a rotatable adjustment shaft manually rotated by a thumb-wheel, the shaft and the thumb-wheel being connected by way of an over-running clutch mechanism configured to allow the thumb-wheel to continue turning while discontinuing rotation of the shaft when the flow control valve actuator is properly positioned in relationship to the flow control valve.

According to a further teaching of the present invention, the processing unit is further interconnected to an alarm unit, the processing unit using data from the pressure sensor to determine activation of the alarm unit.

According to a further teaching of the present invention, the flow actuator, the manual positioning component, the pressure sensor, and the processing unit are housed in a base unit further including a processing unit display, processing unit input keypad, and a power supply.

According to a further teaching of the present invention, the fluid supply assembly, the flow reduction passage, and the flow control valve, are housed in a removable cartridge unit.

There is also provided according to the teachings of the present invention, a fluid drug delivery device comprising: a) a fluid supply assembly; b) a pressure reduction passage having a fluid inlet in fluid communication with the fluid supply assembly, the flow passage also having a fluid outlet; c) a flow control valve interconnected to the fluid outlet; and d) a piezoelectric actuator deployed so as to regulated the flow control valve thereby varying the amount of fluid flowing through the flow control valve.

According to a further teaching of the present invention, there is further included: a) a positioning component deployed so as to position the flow control valve actuator in a predefined spatial relationship to the flow control valve; and b) a processing unit electronically interconnected with a pressure sensor and the flow control valve actuator, the processing unit configured so as to use data from the pressure sensor to determine activation of the flow control valve actuator.

According to a further teaching of the present invention, the positioning component includes a rotatable adjustment shaft manually rotated by a thumb-wheel, the shaft and the thumb-wheel being connected by way of an over-running clutch mechanism configured to allow the thumb-wheel to continue turning while discontinuing rotation of the shaft when the flow control valve actuator is properly positioned in relationship to the flow control valve.

According to a further teaching of the present invention, the processing unit is further interconnected to an alarm unit, the processing unit using data from the pressure sensor to determine activation of the alarm unit.

According to a further teaching of the present invention, the, flow actuator, the manual positioning component, the pressure sensor, and the processing unit are housed in a base unit further including a processing unit display, processing unit input keypad, and a power supply.

According to a further teaching of the present invention, the fluid supply assembly, the flow reduction passage, and the flow control valve, are housed in a removable cartridge unit.

There is also provided according to the teachings of the present invention, a fluid drug delivery device comprising: a) a portable base unit including, a flow actuator, a manual positioning component, at least one pressure sensor, a processing unit, a display, keypad and a power source for the processing unit are housed in a base unit; and b) a cartridge unit that is removably interconnected to the base unit, the cartridge including a fluid supply assembly, a pressure reduction passage, and a flow control valve, the fluid supply assembly providing a pre-pressurized chamber containing a quantity of fluid drug.

According to a further teaching of the present invention, the flow actuator is a piezoelectric actuator deployed so as to regulate the flow control valve thereby varying the amount of fluid flowing through the flow control valve.

According to a further teaching of the present invention, the manual positioning component includes a rotatable adjustment shaft manually rotated by a thumb-wheel, the shaft and the thumb-wheel being connected by way of an over-running clutch mechanism configured to allow the thumb-wheel to continue turning while discontinuing rotation of the shaft when the flow control valve actuator is properly positioned in relationship to the flow control valve.

According to a further teaching of the present invention, the processing unit is electronically interconnected with the pressure sensor and the piezoelectric actuator, the processing unit configured so as to use data from the pressure sensor to determine activation of the piezoelectric actuator.

According to a further teaching of the present invention, the pre-pressurized chamber is accomplished by use of a piston deployed within the chamber so as to define a fluid containment volume within the chamber, a spring element deployed so as press the piston into the fluid containment volume so as to pressurize the quantity of fluid drug supplied within the fluid containment volume.

According to a further teaching of the present invention, the pressure reduction passage is an elongated passageway interconnected to the fluid supply assembly, the elongated passageway having a fluid inlet and a fluid outlet, the elongated passageway configured so as to reduce the pressure in the fluid thereby creating a pressure differential between the fluid inlet and the fluid outlet.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
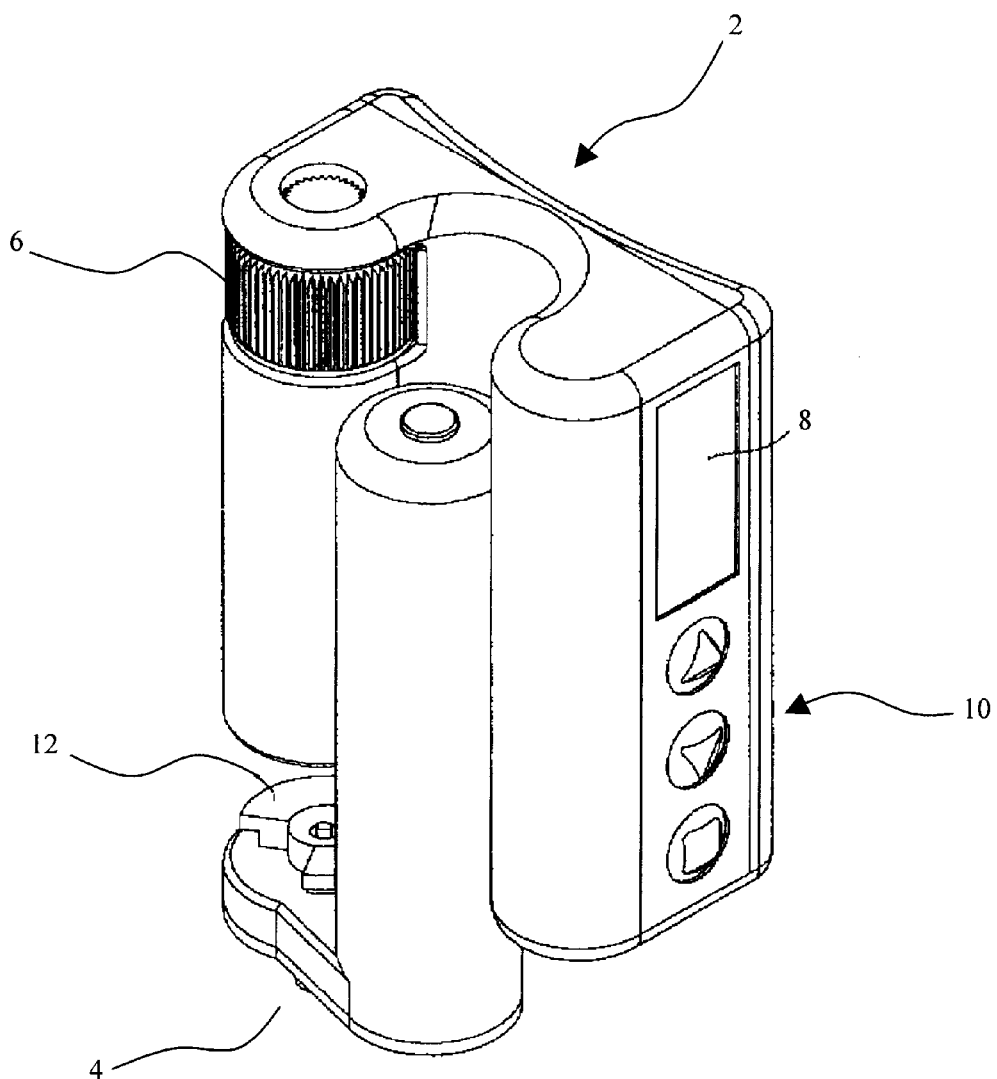
FIG. 1 is an isometric view of a device constructed and operative according to the teachings of the present invention, showing the separated base unit and cartridge unit.

The present invention is portable insulin delivery device.

The principles and operation of a portable insulin delivery device according to the present invention may be better understood with reference to the drawings and the accompanying description.

By way of introduction, the portable insulin delivery device of the present invention houses sensing, processing and regulatory elements, and power source in a base unit. A fluid containment volume, flow path, valve and fluid pressurization assembly are housed in a removable cartridge unit. In the description below and elsewhere in this document, the word "insulin" is used to refer to insulin and any other slow delivery fluid drug or medication.

The insulin is stored in a pressurized fluid containment volume. The pressure forces the insulin out of the containment volume into an elongated flow path, referred to herein as a labyrinth, through a flow control valve and out of the device. There are at least two pressure sensing points located along the labyrinth and a pressure sensor monitors the differential in pressure between the two points. The resultant data is used by a processing unit to determine activation of the flow control valve. The flow control valve is actuated by a piezoelectric actuator controlled by the processing unit. Under normal operating circumstances, the valve is opened just enough to allow the prescribed amount of insulin to flow. This is evidenced by the amount of pressure differential at the two pressure sensing points. If the pressure equalizes, generally indicating a blockage, the piezoelectric actuator opens the valve to allow the full force of the fluid pressure to be applied to the blockage. If the blockage is opened, the differential in pressure will return and the valve is closed back down to the pre-blockage setting. Generally, the valve is open for a few milliseconds. If the pressure remains equal for a predetermined length of time, indicating the blockage has not been opened, the processing unit sounds an alarm and allows the "normally closed" valve to close and discontinue insulin flow.

This configuration offers several advantages over devices of prior art that should be noted here. Firstly, the fluid containment volume, of the present invention, is pressurized before use, herein referred to as "pre-pressurized". This eliminates the need for motor and gear reduction assemblies, of prior art, which are costly, use considerable amounts of energy, and along with needed extra power sources, i.e. batteries, account for a large percentage of the size of devices that use them.

Secondly, monitoring the pressure differential of the insulin pressure in the flow path gives substantially immediate feedback as to the rate of insulin delivery during normal operation. Further, a change in pressure differential would result should a blockage occur.

Thirdly, the present invention's use of a valve to release pressurized insulin so as to control the flow rate of the insulin provides a much more precise and substantially constant delivery of the prescribe dosage, than the rate at which a piston moves through a cylinder used in the prior art.

And fourthly, the pre-pressurized nature of the insulin, in the present invention, is better suited to quickly open blockages. Of further importance is the ability to close the valve after a blockage has been cleared. The mover driven piston devices of prior art use the motor to apply more pressure to the piston, and thus to the insulin, when a blockage occurs. In the devices of prior art, once the blockage is cleared, the pressure build up is dissipated through the fluid outlet of the device and into the patient. This may mean a higher than prescribed dosage level delivered to the patient.

Referring now to the drawings, in FIG. 1 is seen the base unit 2 and the removable cartridge unit 4 separated from each other. A rotatable adjusting wheel 6, colloquially herein referred to as a "thumb-wheel", is used to turn a positioning shaft, which will be discussed below. Also shown, are the processing unit display 8 and keypad 10, and the cartridge unit's portion 12 of the bayonet style quick-connect configuration used to interconnect the two units for operation.

Figure 2:
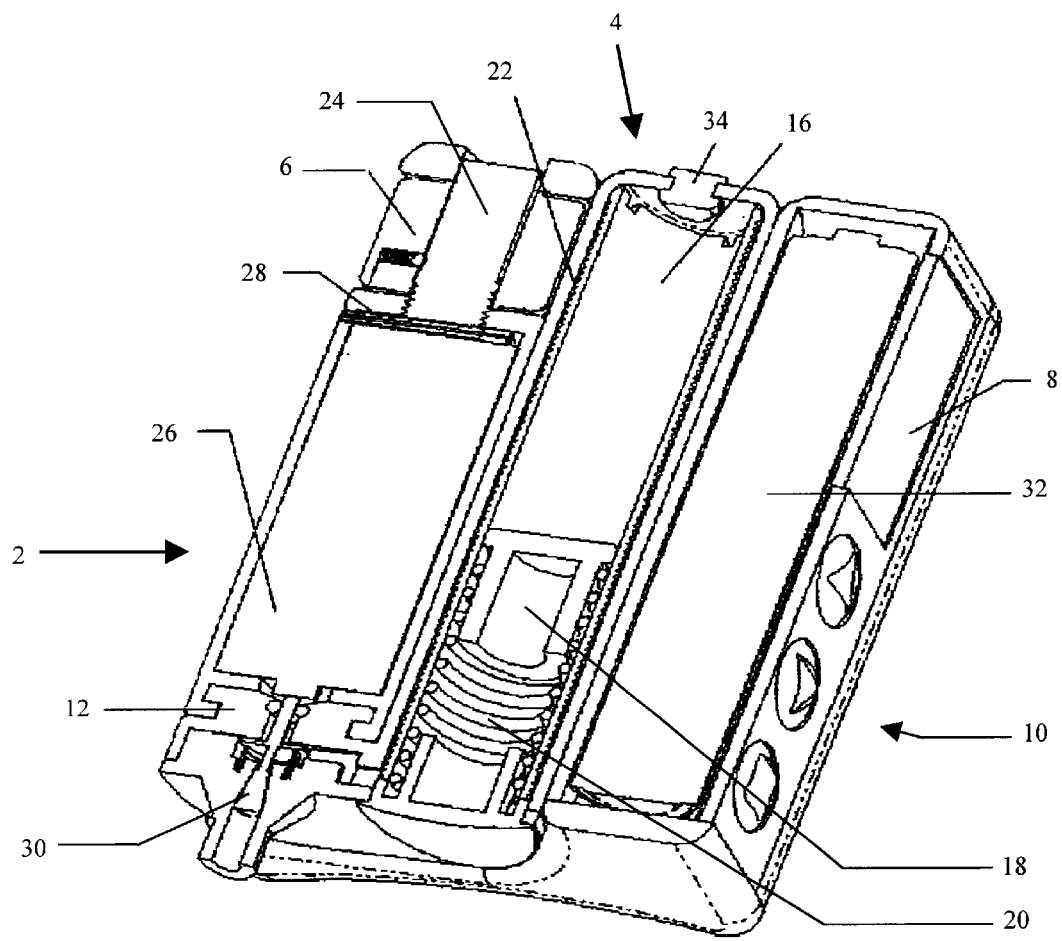
FIG. 2 is an isometric cut-away view of a device constructed and operative according to the teachings of the present invention; which uses a coil spring to bias the piston.

The cut-away isometric view of FIG. 2 provides a perspective of the placement relationship of the components of this embodiment of the present invention. The components are numbered here for reference to the following detailed figures at which point each will be discussed, with the exception of the battery 32, which is the power source for all electrical components and will not be discussed further.

Figure 3:
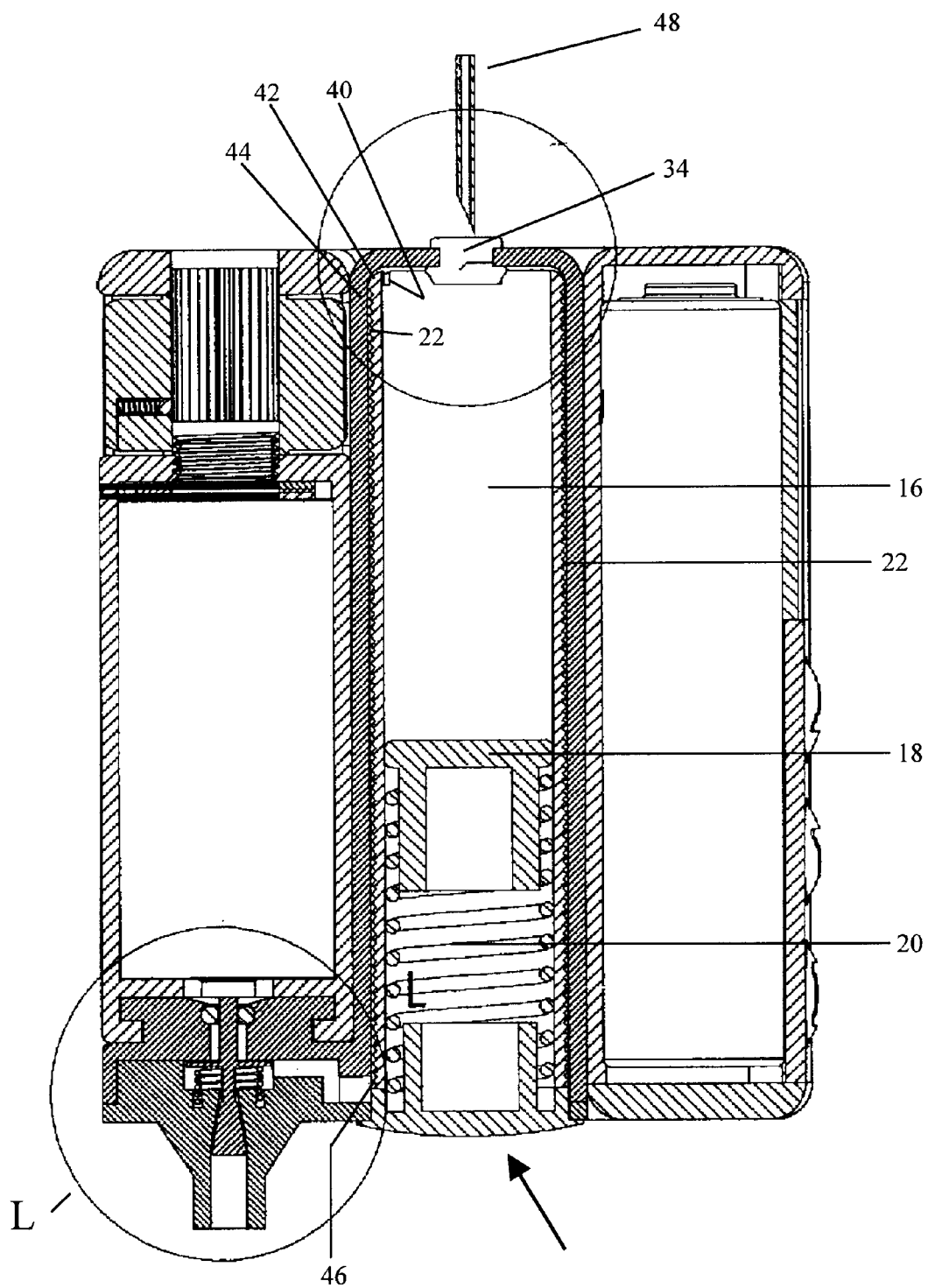
FIG. 3 is a cut-away front view of the preferred embodiment of FIG. 1.

As shown in FIG. 3, the insulin is introduced into the fluid containment volume 16 portion of the cartridge unit by way of a needle 48 that pierces the plug element 34. The needle is generally used in association with a syringe. The insulin is then stored in the fluid containment volume. The piston 18 is biased toward the fluid containment volume by the spring element 20, thereby pressurizing the insulin. During the course of insulin delivery, the spring element will move the piston within the chamber thereby maintaining the pressure. Under force of pressure, the insulin leaves the containment volume by way of a plurality of inlet apertures 40 that lead into an elongated flow passageway 22, herein referred to as a "labyrinth." The labyrinth is formed with a pattern of grooves together with the opposing surface. In the case of a cylindrical passageway, as here, the labyrinth may be produced as an elongated helical flow path around the wall of the fluid containment volume housing 42. This has advantages for the ease of manufacture and level of precision with which the groove can be produced. Optionally, more than one groove 22 can be deployed in a double- or triple-helix, although a single helix is generally preferred. The grooves may be formed on either of first and second cylindrical surfaces 42 or 44. The labyrinth functions to restrict the flow of the insulin such that the viscosity of the insulin together with the size of the passageway will reduce the fluid pressure down line, thus creating pressure differential along the length of the labyrinth. This pressure differential will be discussed at greater length below. It should be noted that while the labyrinth described above is a preferred configuration, any suitable configuration that creates a pressure differential between at least two points in a flow passage is within the intentions of the present invention.

Figure 4:
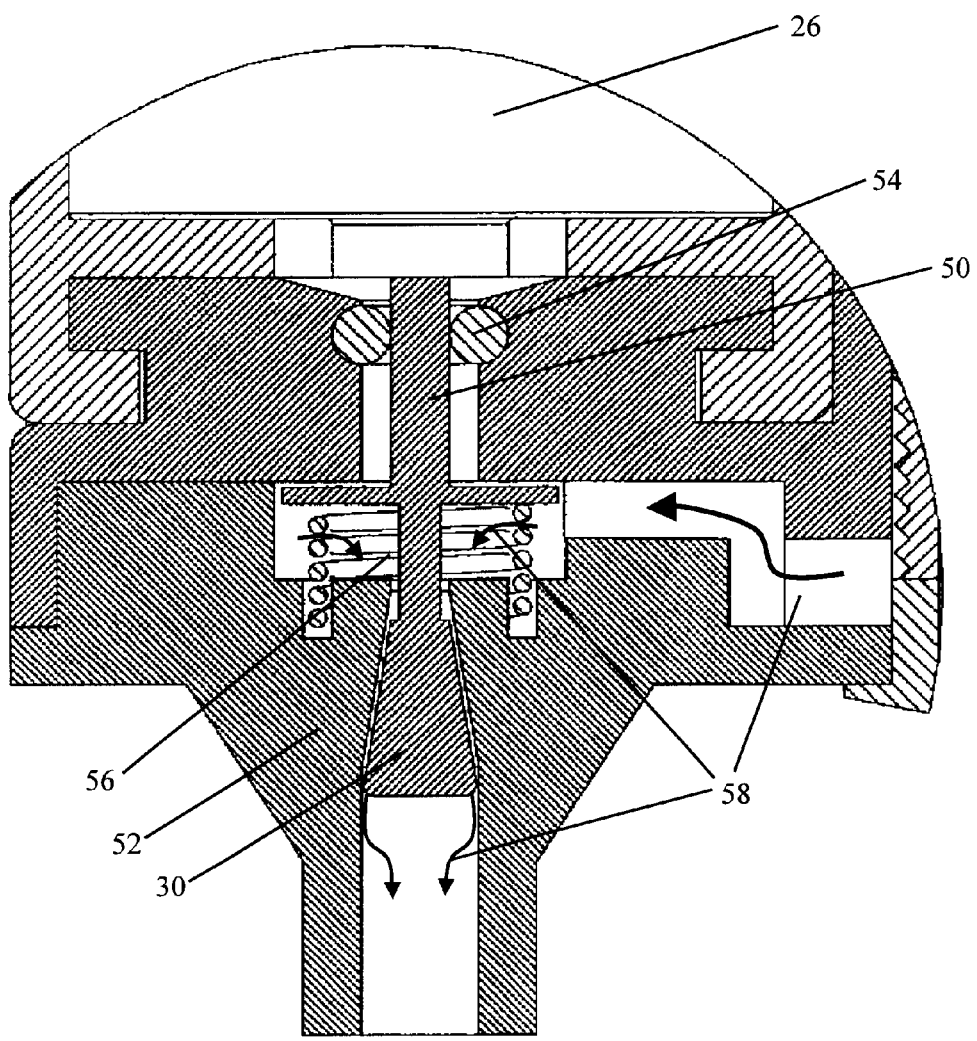
FIG. 4 is a detailed cut-away front view of section L in FIG. 2, showing a flow control valve constructed and operative according to the teachings of the present invention.

The insulin leaves the labyrinth by way of outlet aperture 46, and enters the flow control valve detailed in FIG. 4. The arrows 58 show the flow path of the insulin through the valve assembly. The valve is a conically shaped "normally closed" valve. That is, the spring 56 is pushing against a portion of the valve stem 50 so as to close the valve opening. The valve stem passes through the o-ring 54, which seals the fluid area. The piezoelectric actuator 26 activates the valve by pushing against the valve stem 50, thereby moving the valve body 30 away from the valve housing 52 and allowing insulin to flow. The processing unit controls the piezoelectric actuator so that under normal operating conditions, the valve is open just enough to allow the prescribed amount of insulin flow through the valve. In the case of an equalization of pressure within the labyrinth, usually indicative of a blockage, the piezoelectric actuator opens the valve, thereby allowing the full force of the fluid pressure of the insulin to push against the blockage. Typically, the valve will be open for a few milliseconds. Once the blockage is cleared, the pressure differential indicative of normal operation is reestablished and the valve is closed down to allow only the prescribed amount of insulin to flow. That is, when there is a blockage, the valve will allow the full force of the pressure to act upon the obstruction, however, when the force is not longer needed, the valve closes without allowing substantially any excess insulin flow through the valve to the patient.

Figure 5:
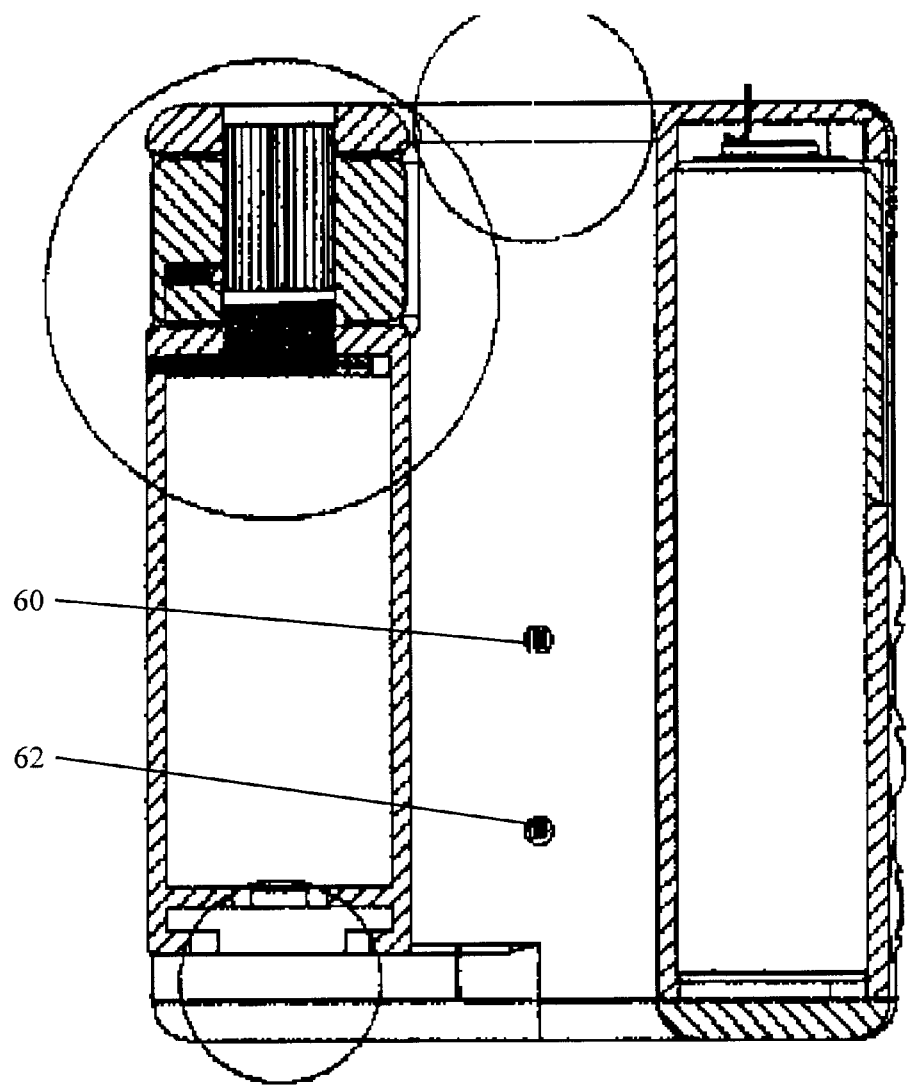
FIG. 5 is a cut-away front view of a base unit constructed and operative according to the teachings of the present invention.

FIG. 5 give a view of the base unit of this embodiment without the cartridge unit connected. Of interest here are the pressure sensing points 60 and 62 whose relationship to the differential pressure sensor and the labyrinth will be discussed in the context of FIGS. 6a and 6b.

Figure 6A:
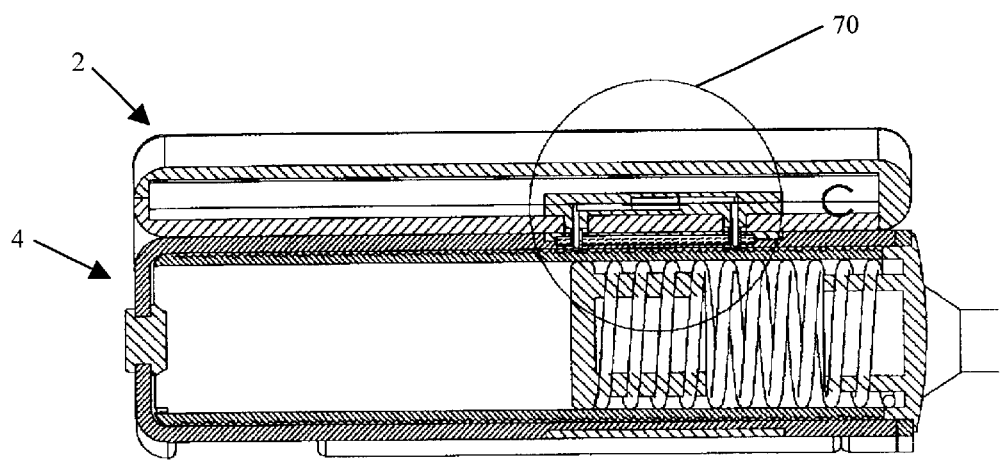
FIG. 6a is a cut-away side view showing a pressure sensing configuration constructed and operative according to the teachings of the present invention.
Figure 6B:
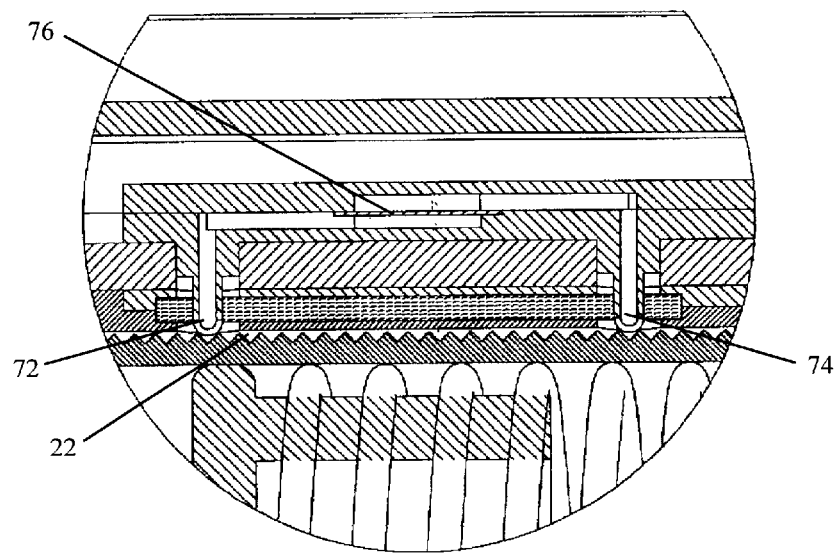
FIG. 6b is a detail of the pressure sensing configuration of FIG. 5.

As seen in the cut-away side view of FIG. 6a the location of the pressure sensing configuration, generally referred to as 70, in the base unit 2 and its relationship to the cartridge unit 4 is readily apparent. Looking now to the detail of FIG. 6b. As the insulin flows through the labyrinth 22, it comes into contact with and applies pressure to a first pressure sensing point 72. Further along the labyrinth the insulin applies pressure to a second pressure sensing point 74. The pressure differential created by the labyrinth is detected and monitored by the differential pressure sensor 76. Even though the two pressure sensing points are relatively close together in the base unit, because of the configuration of the labyrinth, the flow path between the two points is considerably longer so that the pressures that are sensed are at points quite a distance apart. It will be obvious to one skilled in the art that the pressure differential may also be monitored in a variety of ways such as, but not limited to, determining the pressure at each of the pressure sensing points, that data being used by the processor to determine any differential.

Figure 7:
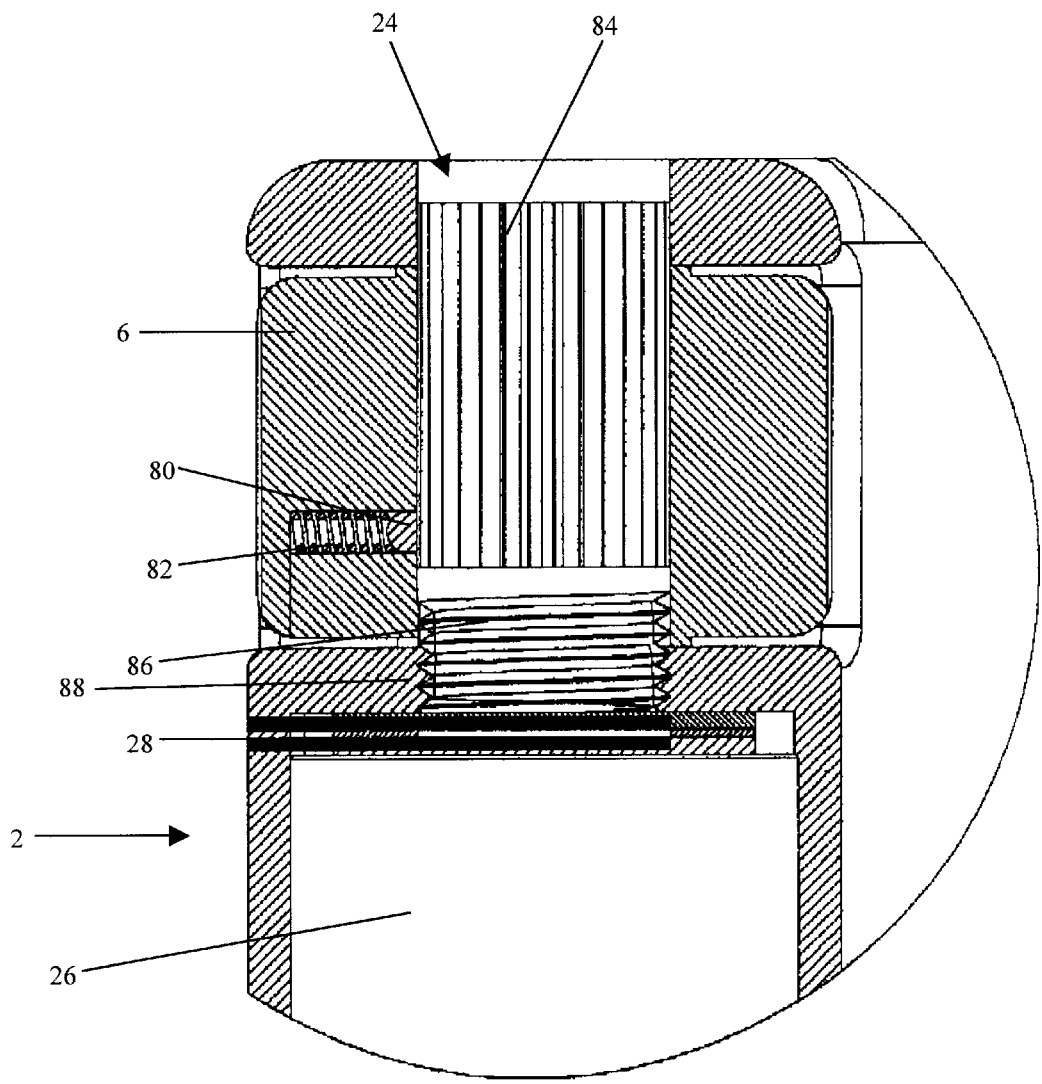
FIG. 7 is a detail of positioning component constructed and operative according to the teachings of the present invention.

In order for the piezoelectric actuator to function properly, it is necessary for it to be in contact with the stem of the flow control valve (see FIG. 4). FIG. 7 is a detail of a positioning component for that purpose as configured for this embodiment of the present invention. The rotatable shaft 24 is divided into two sections, a longitudinally grooved section 84 and a threaded section 86. As the thumb-wheel 6 is turned, a spherical member 80 is pressed into a groove by spring 82 thereby causing the shaft 24 to turn. As the shaft turns, the threads of the threaded section, which are in contact with corresponding threads 88 supplied in the base unit housing 2, cause the shaft to move longitudinally toward the piezoelectric actuator 26. When the piezoelectric actuator contacts the stem of the flow control valve, the shaft continues to move until the contacts of the switch 28 touch, at which point the shaft no longer is able to turn. If the thumb-wheel continues to turn, the spherical element simply jumps out of the groove. The switch 28 therefore, acts as an "on/off" switch not allowing the device to turn "on" until the piezoelectric actuator is properly positioned.

Figure 8:
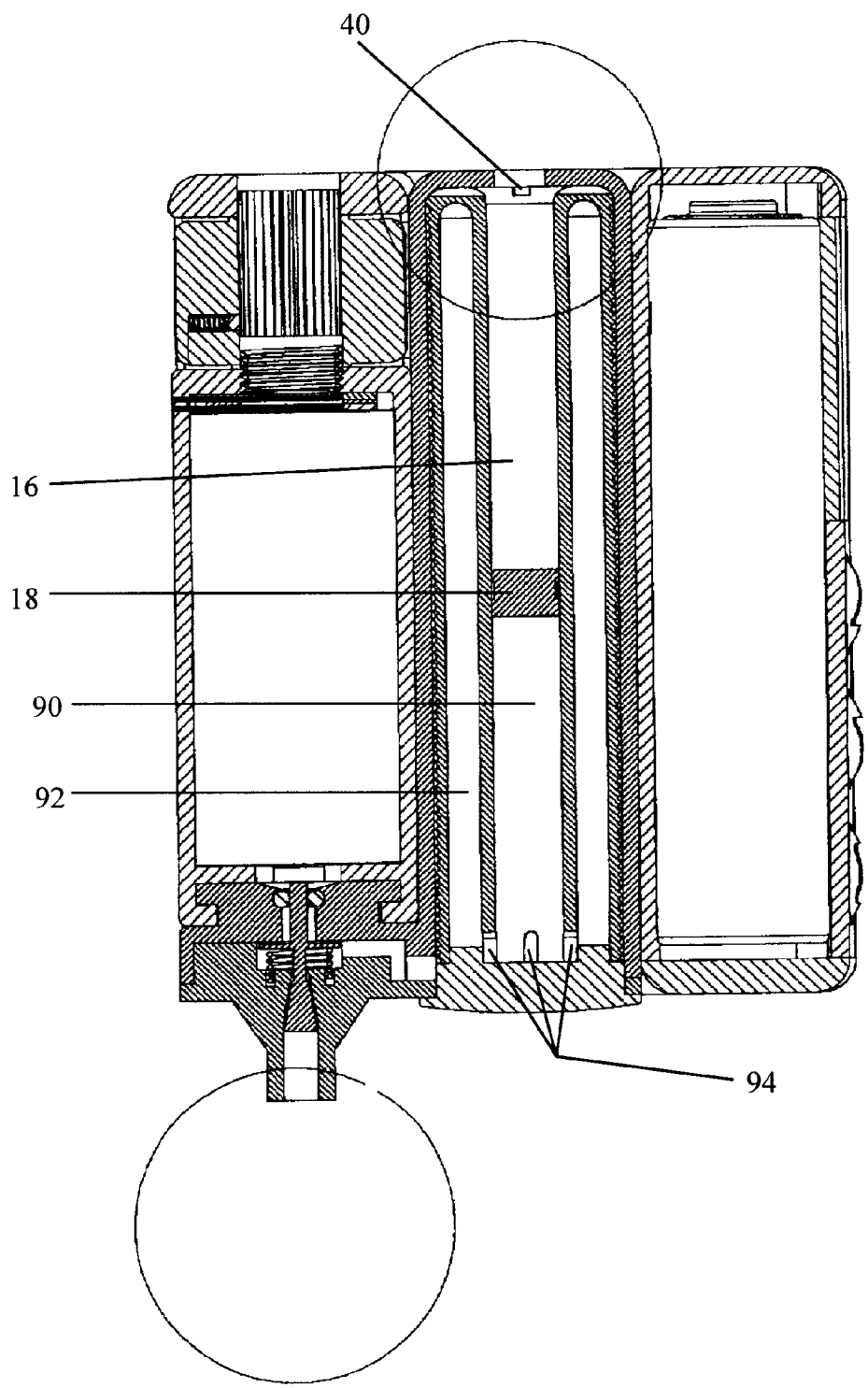
FIG. 8 is a cut-away front view of a device constructed and operative according to the teachings of the present invention, which alternatively uses a pneumatic spring to bias the piston.

FIG. 8 shows a preferred embodiment of the present invention that uses an alternative spring element in the removable cartridge unit. The components of the base unit and some of the cartridge are identical to those discussed above and therefore will not be referred to here. Of interest in this embodiment is the use of a pneumatic spring element to bias the piston 18 toward the fluid containment volume 16. Compressed air is contained within regions 90 and 92 with passages 94 allowing free flow of air between the regions as need. It should be noted that any suitable gas may be used for this purpose Further, although the discussion of spring elements has been limited to coil springs and multi-chambered pneumatic springs, any spring that can be adapted for use in this fashion is within the intention of the present invention and may include, but not be limited to, a plurality of concentric coil springs, pneumatic springs using only one side of the chamber to house the compressed gas, and therefore adding no further "elements" to the device, or elastomeric balloons.

Figure 9:
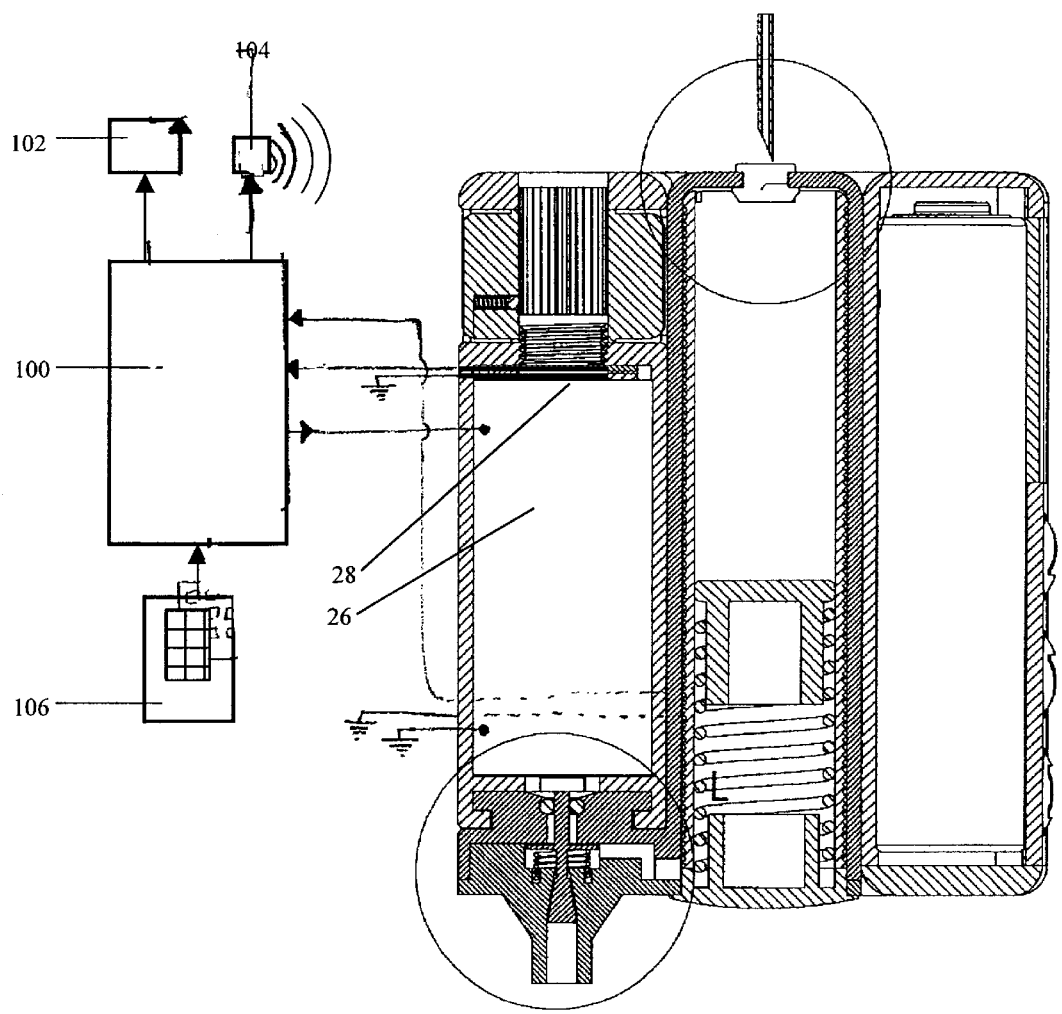
FIG. 9 is a cut-away front view of a device constructed and operative according to the teachings of the present invention together with a schematic of electronic elements.

FIG. 9 shows an embodiment of the present invention identical to that discussed in FIG. 3 and where needed, is numbered accordingly, together with a schematic of the electrical components of that preferred embodiment. The processing unit 100 receives input from: the switch 28, which indicates proper positioning of the piezoelectric actuator; the differential pressure sensor 70 (not shown), which communicates data about the fluid pressure of the insulin; and the keypad 106, which communicates user entered data. The processor sends operational instructions to: the display 102, the piezoelectric actuator 26, which activates the flow control valve; and an alarm 104.

Figure 10:
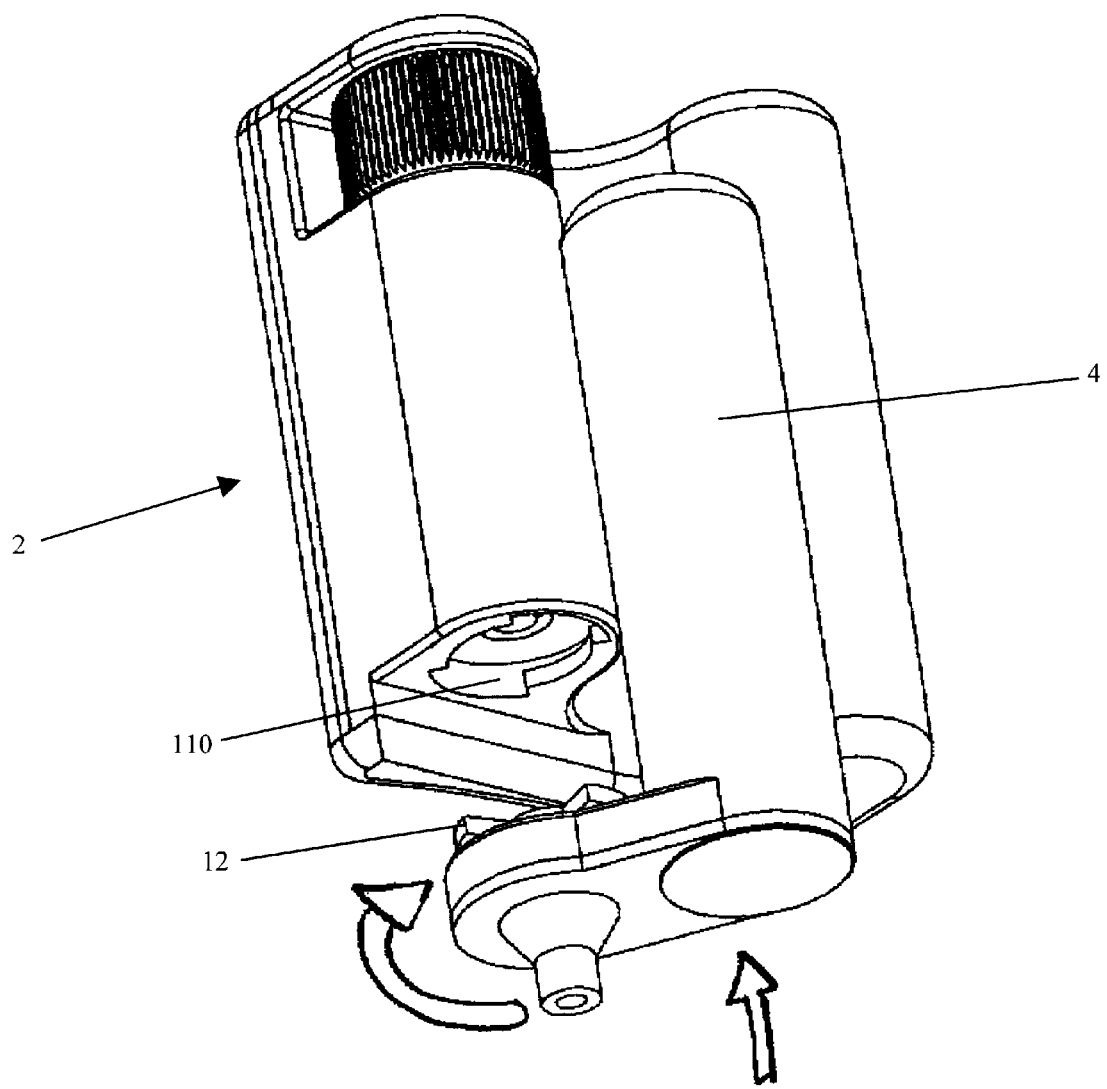
FIG. 10 is an isometric view of a cartridge and base unit constructed and operative according to the teachings of the present invention being joined according to the teachings of the present invention.

FIG. 10 shows the removable cartridge unit separated from base unit of a preferred embodiment of the present invention. Shown are the cartridge unit's portion 12 and the base's portion 110 of the bayonet style quick-connect configuration used to interconnect the units for operation. As the arrows indicate, the cartridge 4 is first inserted into the base 2 and then turned to lock it in place for operation.

Figure 11:
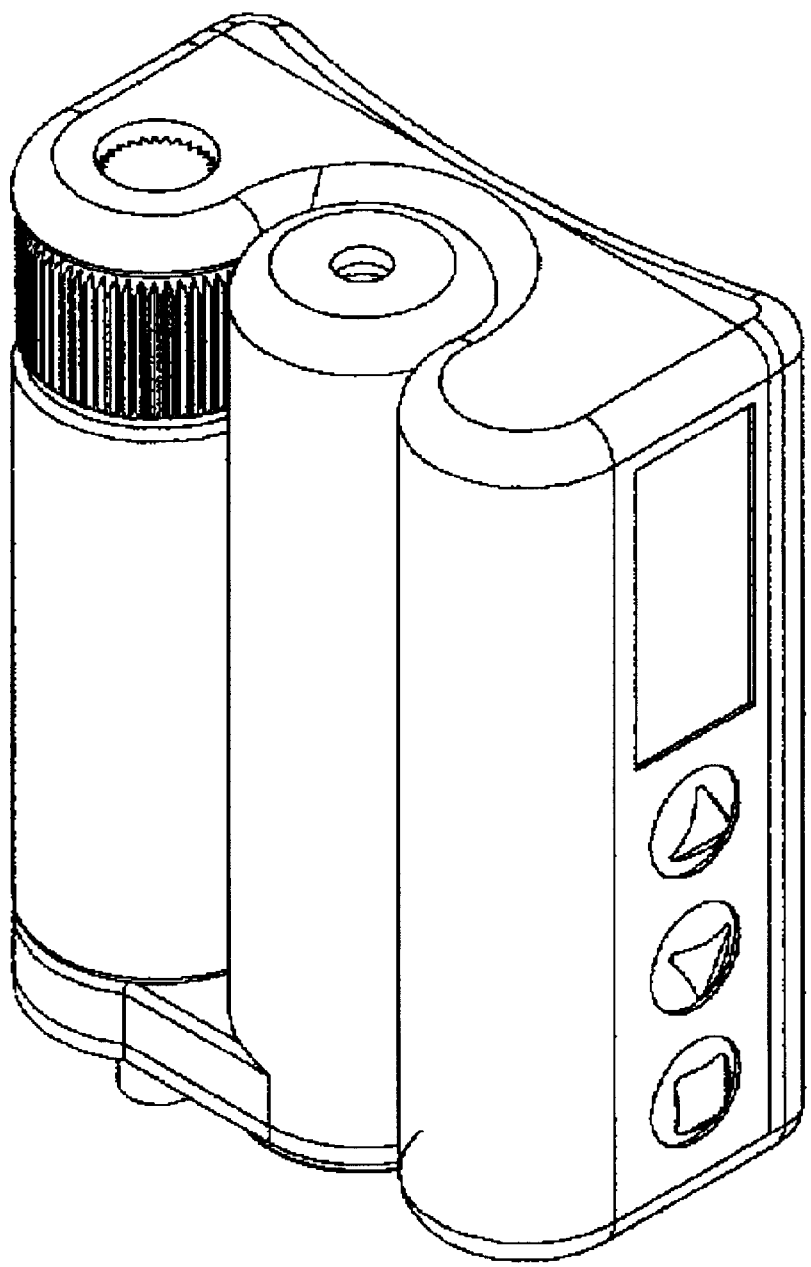
FIG. 11 is an isometric view of a fully assembled device constructed and operative according to the teachings of the present invention.

Finally, FIG. 11 shows a completely assembled preferred embodiment of portable insulin delivery device constructed and operative according to the teachings of the present invention.

It will be appreciated that the above descriptions are intended only to serve as examples, and that many other embodiments are possible within the spirit and the scope of the present invention.

What is claimed is:

1. A fluid drug delivery device comprising:
   (a) a portable base unit including a processing unit, and an actuator controlled by said processing unit;
   (b) a cartridge removably interconnected to said base unit, said cartridge including a fluid supply assembly, a fluid outlet, and a flow control arrangement including a flow control valve, said flow control arrangement controlling flow from said fluid supply assembly to said fluid outlet, wherein said flow control arrangement further includes an elongated pressure reduction passageway; and
   (c) at least one pressure sensor interconnected with a first and a second pressure sensing points, said pressure sensing points located at intervals alone said elongated passageway so as to discern a pressure differential between said first and second pressure sensing points, wherein said flow control valve is operated by force applied to at least one actuation surface provided by said cartridge, said actuation surface being isolated from contact with the fluid, at least part of said actuator being deployable in contact with said actuation surface.

2. The device of claim 1, wherein said portable base unit further includes a retraction mechanism operative to displace said part of said actuator between a deployed position in which said part of said actuator is deployed in contact with said actuation surface and a retracted position in which said part of said actuator is removed from said actuation surface to facilitate interconnection of said cartridge with said base unit and removal of said cartridge from said base unit.

3. The device of claim 2, wherein said retraction mechanism is a manually operable retraction mechanism.

4. The device of claim 2, wherein said retraction mechanism is configured to generate a predefined initial contact pressure between said part of said actuator and said actuation surface.

5. The device of claim 2, wherein said retraction mechanism includes a clutch mechanism deployed to prevent said retraction mechanism from generating an initial contact pressure greater than a predefined maximum initial contact pressure between said part of said actuator and said actuation surface.

6. The device of claim 2, wherein said retraction mechanism includes a switch deployed to detect contact between said part of said actuator and said actuation surface.

7. The device of claim 1, wherein said actuator includes a piezoelectric actuator.

8. The device of claim 1, wherein said fluid supply assembly includes a pressurized chamber containing a quantity of the fluid drug.

9. The device of claim 1, wherein said at least one pressure sensor is electrically associated with said processing unit, said processing unit being responsive to data from said at least one pressure sensor to control said actuator so as to regulate fluid flow to said outlet.

10. The device of claim 1, further comprising an alarm unit associated with said processing unit, wherein said at least one pressure sensor is electrically associated with said processing unit, said processing unit being responsive to data from said at least one pressure sensor to activate said alarm unit on occurrence of at least one predetermined alarm condition.

11. The device of claim 1, wherein said base unit further includes a display and an input keypad both associated with said processing unit.

12. The device of claim 1, wherein said base unit further includes a power source, said processing unit being powered by said power source.

* * * * *